United States Patent
Ozcan et al.

(10) Patent No.: US 11,460,395 B2
(45) Date of Patent: Oct. 4, 2022

(54) SYSTEM AND METHOD FOR MEASURING SERUM PHOSPHATE LEVELS USING PORTABLE READER DEVICE

(71) Applicant: THE REGENTS OF THE UNIVERSITY OF CALIFORNIA, Oakland, CA (US)

(72) Inventors: Aydogan Ozcan, Los Angeles, CA (US); Aniruddha Ray, Toledo, OH (US); Hyouarm Joung, Los Angeles, CA (US); Derek Tseng, Buena Park, CA (US); Isidro B. Salusky, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 244 days.

(21) Appl. No.: 16/900,838

(22) Filed: Jun. 12, 2020

(65) Prior Publication Data

US 2020/0393359 A1 Dec. 17, 2020

Related U.S. Application Data

(60) Provisional application No. 62/861,172, filed on Jun. 13, 2019.

(51) Int. Cl.
*B01L 3/00* (2006.01)
*G01N 21/01* (2006.01)
(Continued)

(52) U.S. Cl.
CPC ........ *G01N 21/01* (2013.01); *B01L 3/502753* (2013.01); *G01N 21/251* (2013.01);
(Continued)

(58) Field of Classification Search
CPC ............. B01L 3/5023; B01L 3/502753; B01L 2300/0681; G01N 21/01; G01N 21/251;
(Continued)

(56) References Cited

U.S. PATENT DOCUMENTS

| 2012/0148141 A1 | 6/2012 | Ozcan et al. |
| 2012/0157160 A1 | 6/2012 | Ozcan et al. |

(Continued)

FOREIGN PATENT DOCUMENTS

| WO | WO 2019/103909 | 5/2019 |
| WO | WO 2019/191697 | 10/2019 |

(Continued)

OTHER PUBLICATIONS

Feng, Juan et al., An improved malachite green assay of phosphate: Mechanism and application, Analytical Biochemistry 409 (2011) 144-149.

(Continued)

*Primary Examiner* — Mark R Gaworecki
(74) *Attorney, Agent, or Firm* — Vista IP Law Group LLP

(57) ABSTRACT

A portable colorimetric assay system includes an opto-mechanical reader configured to be detachably mounted to a mobile phone having a camera or other camera-containing portable electronic device. The opto-mechanical reader includes one or more light sources configured to illuminate a test sample holder and control sample holder disposed in the opto-mechanical reader along an optical path aligned with a camera of the mobile phone or other camera-containing portable electronic device. One or more serum separation membranes are disposed in the opto-mechanical reader and define a sample receiving pad configured to receive a blood sample. A moveable serum collection membrane is membrane is also disposed in the reader and is configured to contact the sample receiving pad in a first (Continued)

position and moveable to a second position where the serum collection membrane is disposed inside the test sample holder.

20 Claims, 11 Drawing Sheets

(51) Int. Cl.
*G01N 21/25* (2006.01)
*G01N 33/49* (2006.01)
*G01N 21/78* (2006.01)
*G01N 21/17* (2006.01)
*G01N 21/84* (2006.01)

(52) U.S. Cl.
CPC .............. *G01N 21/78* (2013.01); *G01N 33/49* (2013.01); *B01L 3/5023* (2013.01); *B01L 2300/0681* (2013.01); *G01N 21/8483* (2013.01); *G01N 2021/0137* (2013.01); *G01N 2021/1776* (2013.01); *G01N 2201/0221* (2013.01); *G01N 2201/104* (2013.01)

(58) Field of Classification Search
CPC .... G01N 21/78; G01N 21/8483; G01N 33/49; G01N 2021/0137; G01N 2021/1776; G01N 2201/0221; G01N 2201/104
See application file for complete search history.

(56) References Cited

U.S. PATENT DOCUMENTS

| | | | |
|---|---|---|---|
| 2012/0218379 A1 | 8/2012 | Ozcan et al. | |
| 2012/0248292 A1 | 10/2012 | Ozcan et al. | |
| 2012/0281899 A1 | 11/2012 | Ozcan et al. | |
| 2013/0092821 A1 | 4/2013 | Ozcan et al. | |
| 2013/0157351 A1 | 6/2013 | Ozcan et al. | |
| 2013/0193544 A1 | 8/2013 | Ozcan et al. | |
| 2013/0203043 A1 | 8/2013 | Ozcan et al. | |
| 2013/0258091 A1 | 10/2013 | Ozcan et al. | |
| 2013/0280752 A1 | 10/2013 | Ozcan et al. | |
| 2014/0120563 A1 | 5/2014 | Ozcan et al. | |
| 2014/0160236 A1 | 6/2014 | Ozcan et al. | |
| 2014/0300696 A1 | 10/2014 | Ozcan et al. | |
| 2015/0111201 A1 | 4/2015 | Ozcan et al. | |
| 2015/0153558 A1 | 6/2015 | Ozcan et al. | |
| 2015/0204773 A1 | 7/2015 | Ozcan et al. | |
| 2016/0070092 A1 | 3/2016 | Ozcan et al. | |
| 2016/0161409 A1 | 6/2016 | Ozcan et al. | |
| 2016/0327473 A1 | 11/2016 | Ozcan et al. | |
| 2016/0334614 A1 | 11/2016 | Ozcan et al. | |
| 2017/0153106 A1 | 6/2017 | Ozcan et al. | |
| 2017/0160197 A1 | 6/2017 | Ozcan et al. | |
| 2017/0168285 A1 | 6/2017 | Ozcan et al. | |
| 2017/0220000 A1 | 8/2017 | Ozcan et al. | |
| 2017/0357083 A1 | 12/2017 | Ozcan et al. | |
| 2018/0003686 A1 | 1/2018 | Ozcan et al. | |
| 2018/0052425 A1 | 2/2018 | Ozcan et al. | |
| 2018/0196193 A1 | 7/2018 | Ozcan et al. | |
| 2018/0373921 A1 | 12/2018 | Di Carlo et al. | |
| 2019/0119737 A1 | 4/2019 | Ozcan et al. | |
| 2019/0137932 A1 | 5/2019 | Ozcan et al. | |
| 2019/0286053 A1 | 9/2019 | Ozcan et al. | |
| 2019/0294108 A1 | 9/2019 | Ozcan et al. | |
| 2019/0316172 A1 | 10/2019 | Ozcan et al. | |
| 2019/0333199 A1 | 10/2019 | Ozcan et al. | |
| 2019/0346369 A1 | 11/2019 | Ozcan et al. | |
| 2020/0103328 A1 | 4/2020 | Ozcan et al. | |

FOREIGN PATENT DOCUMENTS

| | | |
|---|---|---|
| WO | WO 2019/200289 | 10/2019 |
| WO | WO 2019/236569 | 12/2019 |
| WO | WO 2020/018154 | 1/2020 |

OTHER PUBLICATIONS

Joung, Hyou-Arm et al., Point-of-Care Serodiagnostic Test for Early-Stage Lyme Disease Using a Multiplexed Paper-Based Immunoassay and Machine Learning, ACS Nano 2020, 14, 229-240.

Berg, Brandon et al., Cellphone-Based Hand-Held Microplate Reader for Point-of-Care Testing of Enzyme-Linked mmunosorbent Assays, ACS Nano, vol. 9, No. 8, 7857-7866, 2015, www.acsnano.org.

Berg, Brandon et al., Cellphone-Based Hand-Held Microplate Reader for Point-of-Care Testing of Enzyme-Linked Immunosorbent Assays, ACS Nano, vol. 9, No. 8, 7857-7866, 2015, www.acsnano.org.

Coscun, Ahmet F. et al., A personalized food allergen testing platform on a cellphone, Lab Chip. Feb. 21, 2013; 13(4): 636-640 doi:10.1039/c2lc41152k.

Feng, Steve et al., High-throughput and automated diagnosis of antimicrobial resistance using a cost-effective cellphone-based microplate reader, Scientific Reports, 6:39203, DOI:10:1038/srep39203 2016.

Joh, Daniel Y. et al., Inkjet-printed point-of-care immunoassay on a nanoscale polymer brush enables subpicomolar detection of analytes in blood, www.pnas.org/cgi/doi/10.1073/pnas.1703200114 2017.

Koydemir, Hatice Ceylan et al., Smartphones Democratize Advanced Biomedical Instruments and Foster Innovation, Clinical Pharmacology & Therapeutics, vol. 00, No. 00, Month 2018, www.cpt-journal.com (4 pages).

Koydemir, Hatice Ceylan et al., Comparison of supervised machine learning algorithms for waterborne pathogen detection using mobile phone fluorescence microscopy, Nanophotonics 2017; 6(4): 731-741.

Hernandez-Neuta, I. et al., Smartphone-based clinical diagnostics: towards, democratization of evidence-based health care, Journal of Internal Medicine, 2019, 285; 19-39.

Coskun, Ahmet F. et al., Albumin testing in urine using a smartphone, Lab Chip. Nov. 7, 2013; 13(21): 4231-4238. doi:10.1039/c3lc50785h.

Wei, Qingshan et al., Detection and Spatial Mapping of Mercury Contamination in Water Samples Using a Smart-Phone, ACS Nano, vol. 8, No. 2, 1121-1129, 2014, www.acsnano.org.

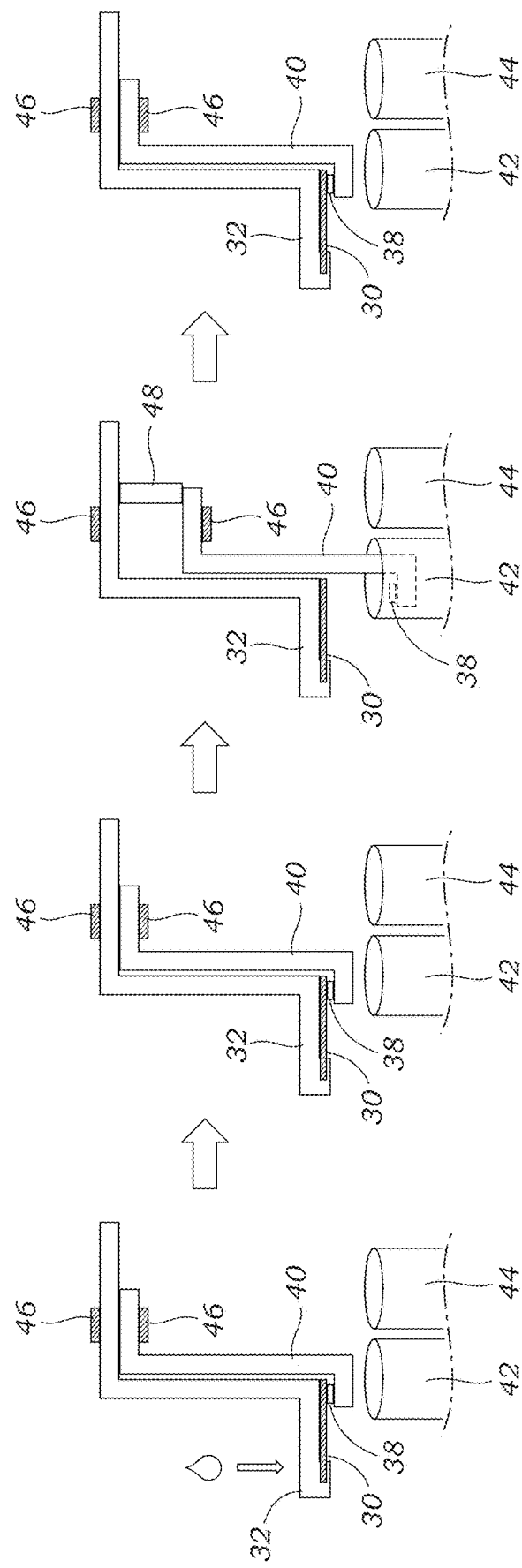

SYSTEM AND METHOD FOR MEASURING SERUM PHOSPHATE LEVELS USING PORTABLE READER DEVICE

RELATED APPLICATION

This application claims priority to U.S. Provisional Patent Application No. 62/861,172 filed on Jun. 13, 2019, which is hereby incorporated by reference in its entirety. Priority is claimed pursuant to 35 U.S.C. § 119 and any other applicable statute.

STATEMENT REGARDING FEDERALLY SPONSORED RESEARCH AND DEVELOPMENT

This invention was made with government support under Grant Number EEC-1648451, awarded by the National Science Foundation and Grant Number DK104687, awarded by the National Institutes of Health. The government has certain rights in the invention.

TECHNICAL FIELD

The technical field generally to portable or mobile sensor devices for measuring the quantity of an analyte in blood serum of a mammal. In particular, the technical field relates to a portable or mobile colorimetric reader device that is used to measure serum phosphate levels in the blood of a mammalian subject.

BACKGROUND

Phosphate is one of the most important analytes in blood as it is essential for multiple functions, including e.g., energy exchange, membrane transport, and intracellular signal transduction. Phosphate ions are used by the body to carry out metabolic processes such as the production and storage of energy, buffering of blood, regulation of gene transcription, and enabling the transduction of signals that regulate pathways which affect organ functions in different endocrine systems. The normal serum phosphate concentration generally ranges between 2.5-5.6 mg/dl in healthy adults, and values are age dependent in children. The maintenance of normal serum phosphate levels is regulated by a complex system that includes organ cross-talk between the intestines, kidney, bone, and parathyroid glands. Such interactions affect intestinal absorption, reabsorption and excretion by the kidneys, and the flux of phosphate between extracellular and skeletal pools. Hypophosphatemia and hyperphosphatemia may give rise to a number of skeletal abnormalities, cardiovascular diseases, and impairments in muscular function. Humans with rare specific genetic mutations develop hypophosphatemia (hypophosphatemic rickets) or hyperphosphatemia (i.e., tumoral calcinosis).

However, the most common cause of elevated serum phosphate levels is chronic kidney disease (CKD). CKD is a significant problem that can affect both children and adults, and is characterized by progressive, irreversible deterioration of kidney function that ultimately leads to end stage renal disease (ESRD) and the need for dialysis and renal transplantation. Several studies have demonstrated that disturbances in serum phosphate homeostasis increase when glomerular filtration rate (GFR) decreases below 60 ml/min/ 1.73 m$^2$. As of 2013, more than 468,000 patients with ESRD were being treated with some form of dialysis treatment in the USA. Several epidemiological studies have highlighted associations between serum phosphate levels and vascular calcifications, cardiovascular morbidity, and overall mortality—not only in patients treated with dialysis, but also in those with early stages of CKD. In addition, studies in humans with normal renal function have shown that even small increases in serum phosphate levels are associated with increased morbidity and mortality. It has also been established that phosphate induces vascular calcification and endothelial dysfunction; thus, there is clear evidence that phosphate promotes trans-differentiation of vascular smooth muscle cells to a chondro-osteoblast like phenotype. Indeed, hyperphosphatemia is an independent risk factor for the progression of cardiovascular disease. Currently, prevention and treatment of hyperphosphatemia with diet and phosphate binders is the cornerstone strategy recommended for patients with CKD. Although enteral phosphate binders are effective, one of the major problems is poor compliance due to frequent administration (up to 3-5 times daily) and pill burden. Despite the overwhelming evidence of phosphate toxicity in CKD, serum phosphate levels are monitored only once or twice per month in dialysis patients and every 3-6 months in non-dialysis CKD patients.

Despite the emerging medical advances in dialysis technology in the 21$^{st}$ century and more than $22 billion per year in expenditures, the mortality rates of ESRD patients remain elevated. Therefore, ESRD remains an area where more effective treatment and monitoring technologies are critically needed. This is especially important for children and young adults that lack the traditional risk factors associated with cardiovascular disease. Thus, elevated serum phosphate levels represent an important health issue and a clear morbidity and mortality risk.

Currently, serum phosphate determinations are performed in laboratory settings that require bulky and expensive photometric and/or electro-chemiluminescence equipment. There is a need to develop tools to empower patients and families to monitor serum phosphate levels at home, or in resource-limited settings, in order to promote close monitoring of phosphate levels in response to dietary changes, and to better inform phosphate binder management. Such an approach has been very successfully applied for the monitoring of serum glucose in patients with diabetes. Indeed, the wide application of this home-based glucose sensing technology has markedly improved clinical outcomes in diabetes management. There is a strong clinical need for an analogous field-portable, reliable, and cost-effective serum phosphate sensing device that can potentially be used even at home.

SUMMARY

A portable and cost-effective phosphate sensing system is disclosed herein that operates in connection with a mobile phone (e.g., Smartphone) with a custom-designed opto-mechanical attachment and, in one embodiment, an integrated paper-based microfluidic chip for measuring serum phosphate levels. The phosphate sensing device requires a small volume of blood and a paper-based disposable chip is used for serum separation from blood. This separated serum is then tested using a colorimetric assay that is integrated into the opto-mechanical attachment mounted onto the camera unit of the Smartphone or other portable electronic device. A Smartphone program or application (i.e., "app") is executed on the Smartphone and is used to analyze and quantify the phosphate concentration in blood using a ratiometric analysis and a calibration curve, which was validated using a standard laboratory-grade multi-analyte auto-analyzer. Each measurement, from the beginning to the end, takes ~45 min to complete and requires only ~20-50 μL of whole blood from the patient. This point-of-care (POC) device was further tested using blood samples taken from patients before and during hemodialysis, providing a strong correlation with the ground truth laboratory tests performed on the same samples.

In an alternative embodiment to the paper-based microfluidic chip, a microfluidic chip using one or more microfluidic channels or capillaries may be used to separate serum from whole blood. The separated serum may then pass to a reaction chamber, well, or region in the microfluidic chip where can be optically interrogated using the reader device that is secured to the Smartphone or other portable electronic device. For example, a portable colorimetric assay system may include an opto-mechanical reader configured to detachably mounted to a mobile phone, the opto-mechanical reader comprising one or more light sources configured to illuminate a test sample region of a microfluidic chip and control sample region of the microfluidic chip, the microfluidic chip disposed in the opto-mechanical reader along an optical path aligned with a camera of the mobile phone. The system further includes a microfluidic chip, which is removably disposed in the opto-mechanical reader, and configured to receive a blood sample and separate blood serum from the blood sample into the test sample region of the microfluidic chip. The microfluidic chip may be insertable/removable from the opto-mechanical reader.

In one embodiment, a portable colorimetric assay system includes an opto-mechanical reader configured to be detachably mounted to a mobile phone or other camera-containing portable electronic device, the opto-mechanical reader comprising one or more light sources configured to illuminate a test sample holder having assay reagent(s) contained therein and control sample holder (e.g., separate wells, vials, or the like) disposed in the opto-mechanical reader along an optical path aligned with a camera of the mobile phone or other camera-containing portable electronic device. One or more separation membranes that form a sample receiving pad are disposed in the opto-mechanical reader and are configured to receive a blood sample. The opto-mechanical reader further includes a moveable serum collection membrane (in a separate moveable holder) that is configured to contact the sample receiving pad in a first position and disposed inside the test sample holder when moved to a second position. In one embodiment, the moveable serum collection membrane is biased against the sample receiving pad using biasing means. A shim or spacer can be used to hold the serum collection membrane in the test sample holder (in the second position) for incubation/reaction and then removed. Light illuminates the test sample holder and the control sample holder and images of light passing through these respective sample and control holders is captured by the camera of the mobile phone. Software or the application in the Smartphone or other computing device then calculates a ratio of the light intensity of the images of the test sample holder and the control holder and is then converted to a concentration. The software may use only a single image to calculate the ratio or multiple images. For example, multiple images may be used to calculate a mean or average ratio.

In another embodiment, a method of using the portable colorimetric assay system includes: loading a blood sample onto the sample receiving pad; contacting the moveable serum collection membrane with the sample receiving pad in the first position; moving the moveable serum collection membrane to a second position within the test sample holder; maintaining the moveable serum collection membrane for an elapsed period of time to react the contents of the sample holder with one or more reagents contained in the test sample holder; illuminating the test sample holder and the control sample holder with the one or more light sources; acquiring one or more images of the test sample holder and the control sample holder with the camera of the mobile phone or other camera-containing portable electronic device; and calculating a concentration of an analyte contained in the test sample holder based on a ratio of the intensity of light in the one or more images of the test sample holder and the control sample holder.

In another embodiment, a method of using the portable colorimetric assay system includes: loading a blood sample into the microfluidic chip; illuminating the test sample region and control sample region with the one or more light sources; acquiring one or more images of the test sample region and control sample region with the camera of the mobile phone or other camera-containing portable electronic device; and calculating a concentration of an analyte contained in the test sample based on a ratio of the intensity of light in the one or more images of the test sample region and control sample region.

BRIEF DESCRIPTION OF THE DRAWINGS

FIGS. 3A-3D illustrates a schematic illustrate of the operations or steps of serum separation and assay. FIG. 3A illustrates the deposition of the blood on the chip. FIG. 3B illustrates serum separation and collection in the collection pad. FIG. 3C illustrates the collection pad is submerged into a well containing water and reagents. The collection pad is lowered manually but is held in place using an adaptor. FIG. 3D illustrates how following the incubation period, the adaptor is manually removed and the collection unit gets retracted back due to a magnetic force.

DETAILED DESCRIPTION OF THE ILLUSTRATED EMBODIMENTS

Figure 1A:
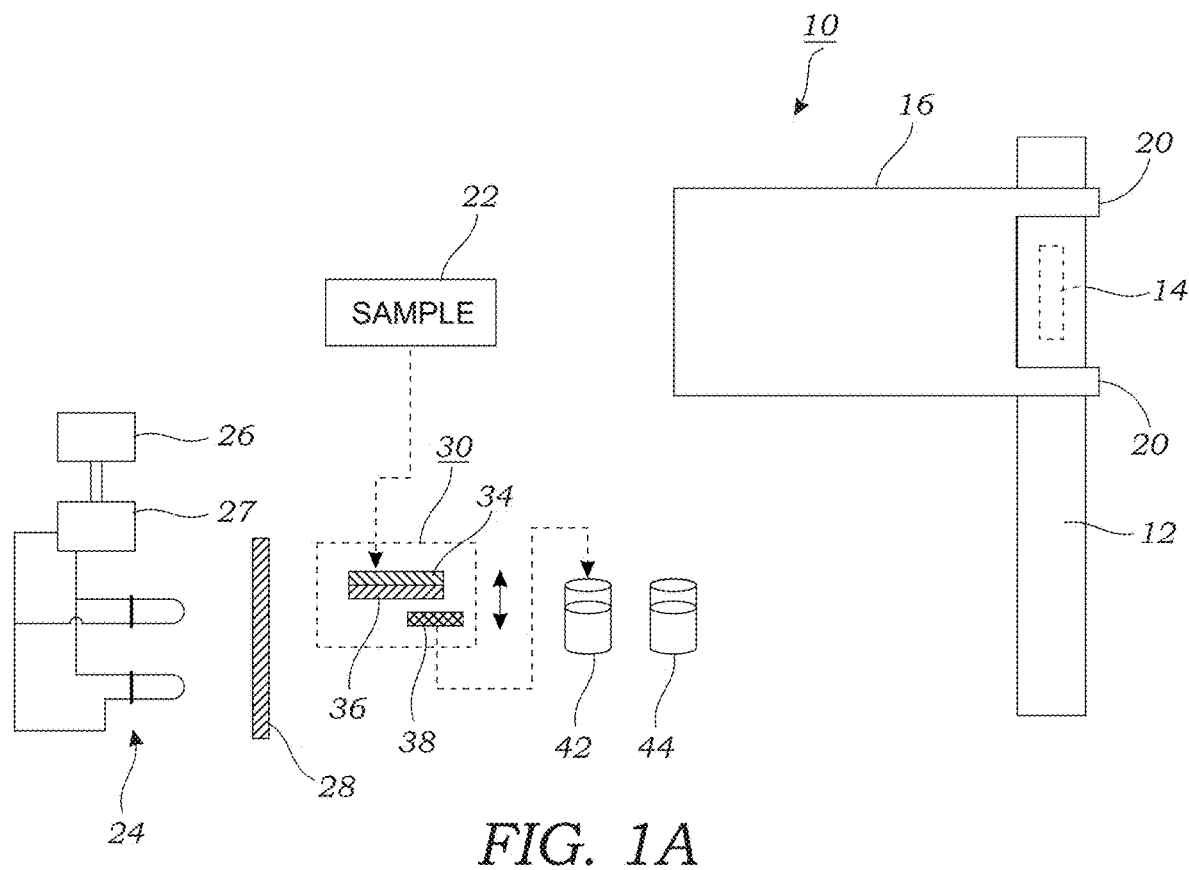
FIG. 1A schematically illustrates one embodiment of a system for measuring the concentration of an analyte in blood serum (e.g., phosphate) using a modular reader device that attaches to a mobile phone (e.g., Smartphone).
Figure 1B:
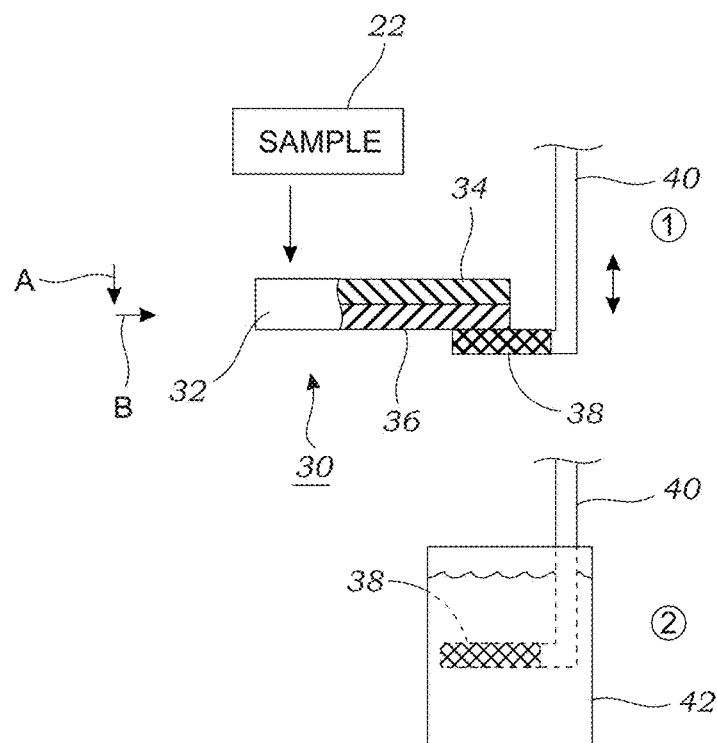
FIG. 1B illustrates a paper-based chip according to one embodiment along with a serum collection membrane disposed on a moveable holder. The moveable holder can selectively place the serum collection membrane in contact with one side of the paper-based chip or inside a test sample holder (e.g., well).
Figure 1C:
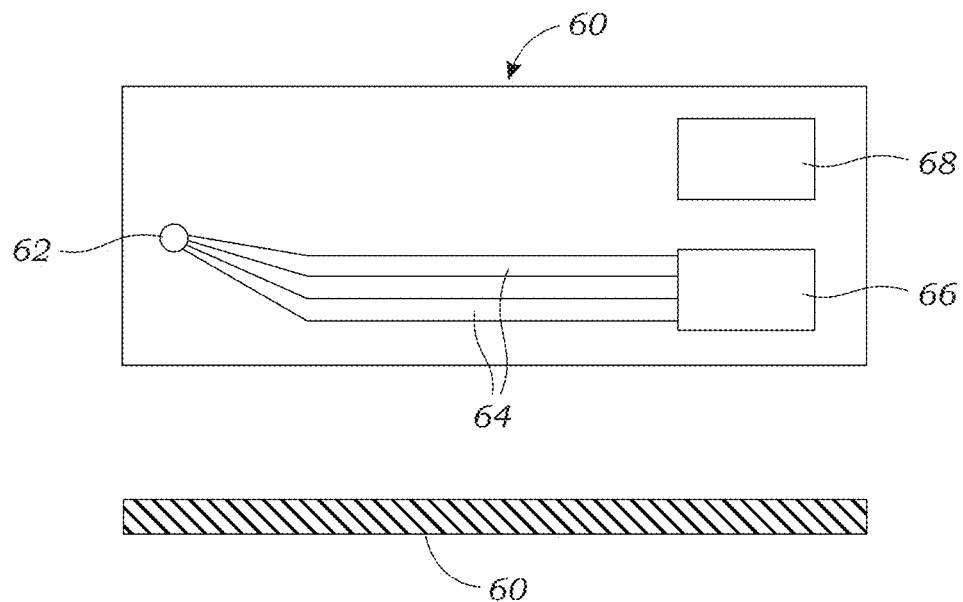
FIG. 1C illustrates top and side views of single microfluidic chip according to another embodiment.
Figure 1D:
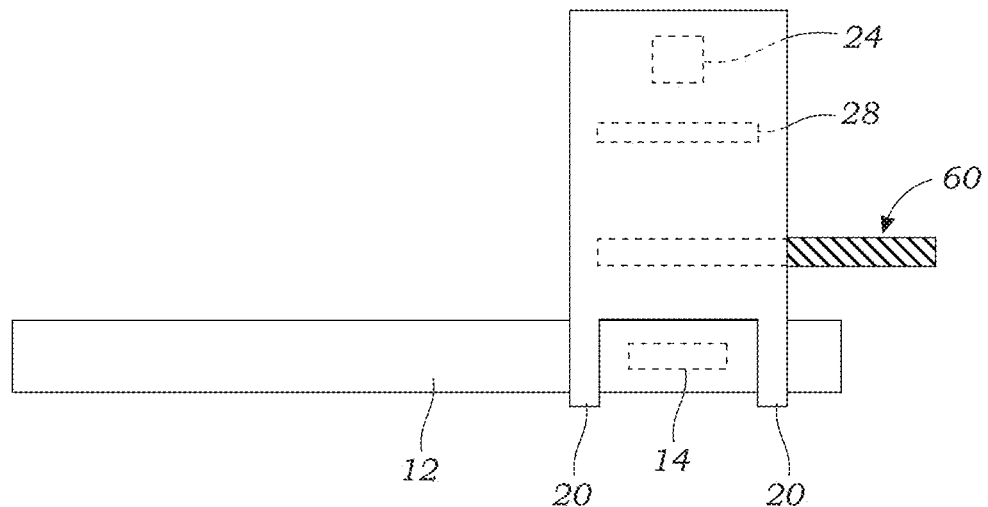
FIG. 1D illustrates an alternative embodiment of the modular reader device is used with the microfluidic chip of FIG. 1C.
Figure 1E:
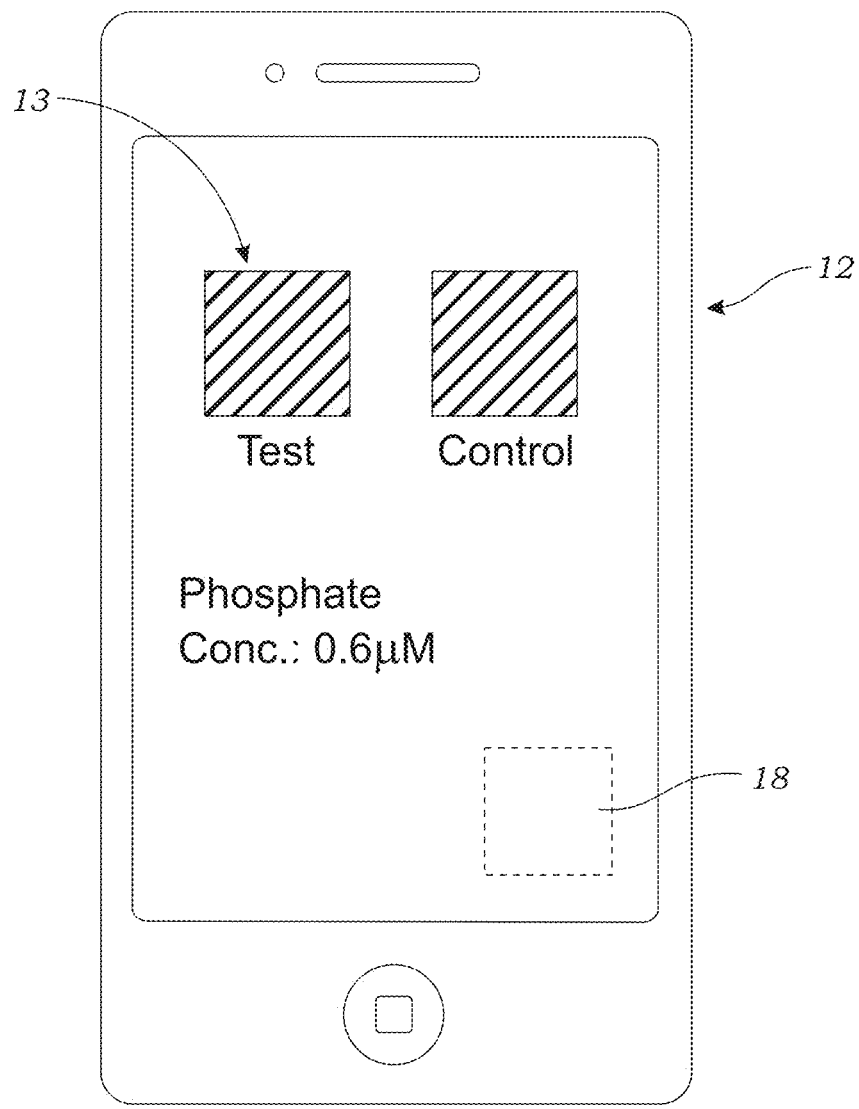
FIG. 1E illustrates the display of the mobile phone device running a software application or "app" that is used to test the sample and display an image of the test and control holders and the results thereon.
Figure 1F:
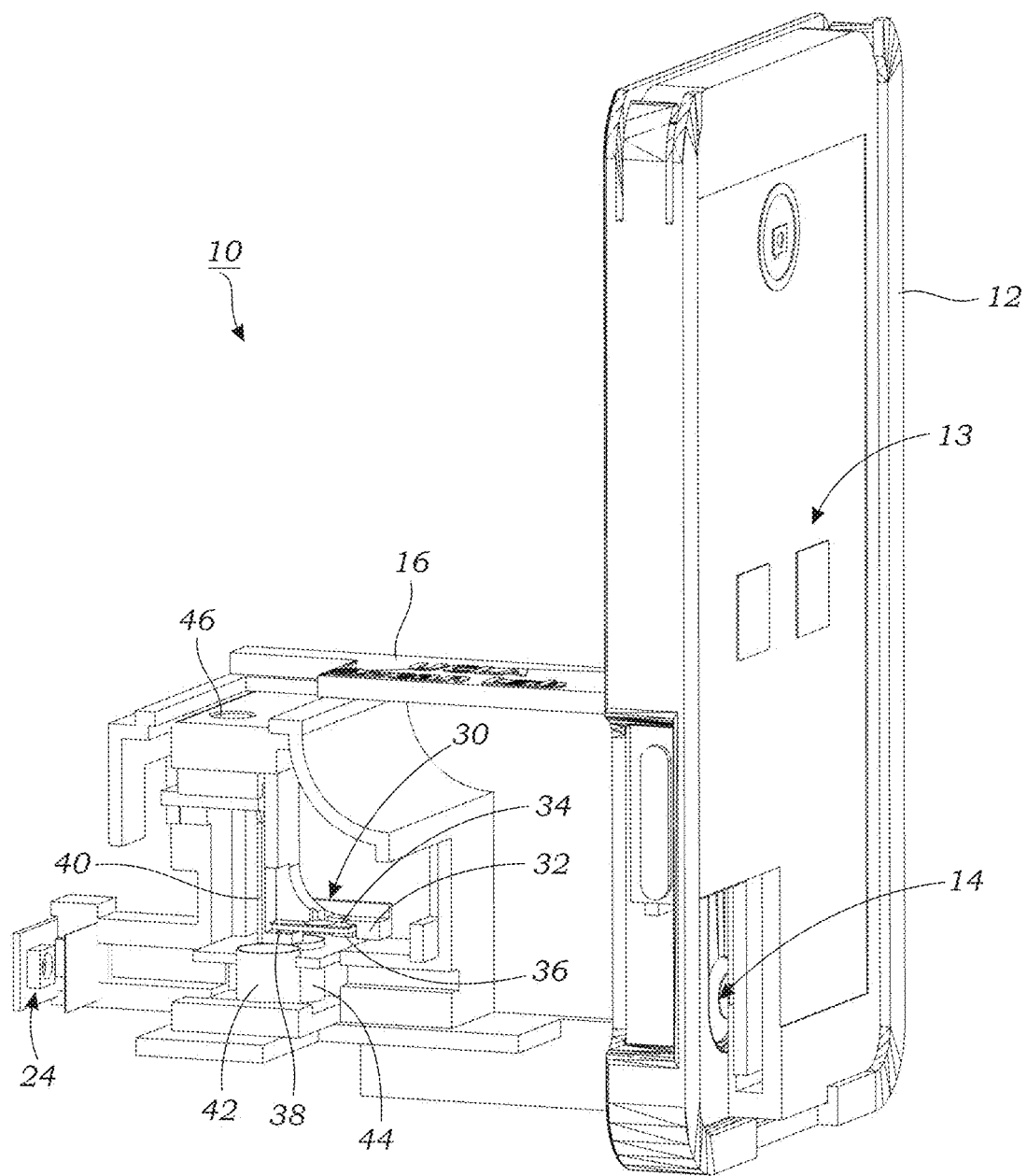
FIG. 1F illustrates a perspective view of the system with a mobile phone secured to the opto-mechanical reader device.
Figure 1G:
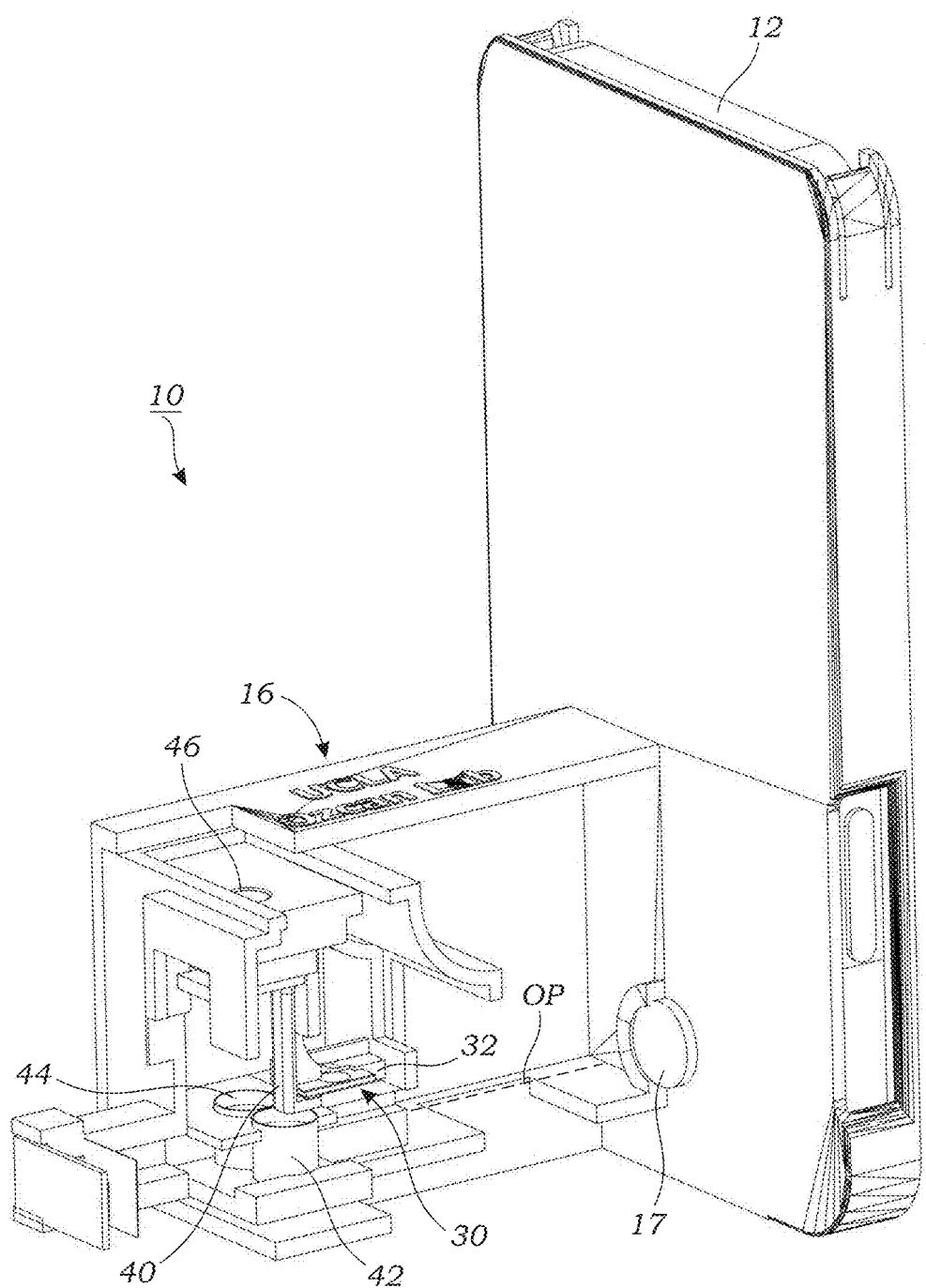
FIG. 1G illustrates another perspective view of the system with a mobile phone secured to the opto-mechanical reader device. An optical path places the test and control holders (e.g., wells) between a light source, diffuser, and internal lens.
Figure 1H:
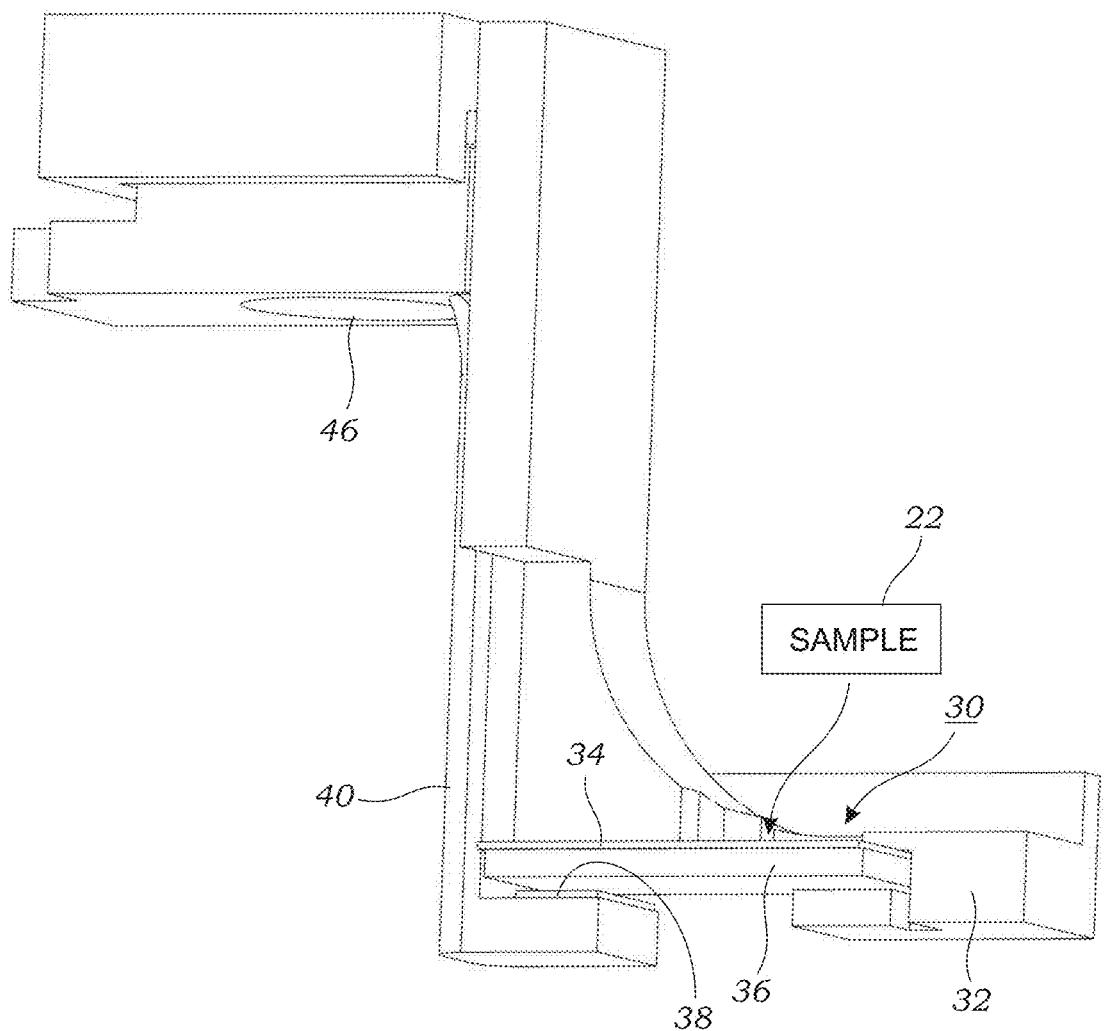
FIG. 1H illustrates a perspective view of the paper-based chip and the moveable holder that contains a collection membrane and is used to move the same between a first position in contact with the chip and a second position that places the collection membrane in a test sample holder (e.g., well).

FIGS. 1A, 1F, and 1G illustrate one embodiment of a portable or mobile based system 10 for measuring the concentration of an analyte such as phosphate within the blood serum (or other bodily fluid) of a mammalian subject. The system 10 includes a portable electronic device 12 with a camera 14 such as a Smartphone mobile phone. The portable electronic device 12 may also include other mobile or portable electronic devices 12 having a camera 14. This may include web cams, tablet PCs, personal digital assistants, or even digital cameras. The system 10 includes a modular opto-mechanical reader device 16 that is secured to the portable electronic device 12 to place the camera 14 of the portable electronic device 12 within an optical path that is used to capture color images 13 of a sample and control as described below. Taken together, the opto-mechanical reader device 16 and the portable electronic device 12 and application or software 18 executed on the portable electronic device 12 operate together as a sensor to detect the concentration of analytes such as serum phosphate concentration.

The opto-mechanical reader device 16 may have fasteners 20 such as tabs, clips, slots, or the like to enable to opto-mechanical reader device 16 to be temporarily secured to the portable electronic device 12. The opto-mechanical reader device 16 may be broken into multiple sub-units or components that are secured to one another during assay measurements. For example, one sub-unit of the reader device 16 may house the portable electronic device 12 while another houses the optical components and assay-based components as discussed herein. As seen in FIGS. 1A, 1B, 1F, 1G, 1H a paper-based microfluidic chip 30 is provided, which can efficiently separate serum from small quantities of blood. This paper-based blood separation chip 30 includes a holder 32 that supports or contains a first serum separation membrane 34 (e.g., Fusion 5) and a second separation membrane 36 (e.g., asymmetric polysulfone) that filters-out red blood cells and the like. The first serum separation membrane 34 allows fluid flow in the vertical direction as seen by arrow A in FIG. 1B while the second separation membrane 36 allows flow in the lateral or horizontal direction as seen by arrow B in FIG. 1B. Collectively, the two membrane 34, 36 may sometimes be referred to herein as sample receiving pad. A moveable serum collection membrane 38 (also referred to herein as a sample collection pad 38), which may also be considered part of the chip 30, is used to collect serum from the second separation membrane 36 (or sample receiving pad). As explained herein, the moveable serum collection membrane 38 is, depending on the state of the test or assay, in physical contact with the second separation membrane 36 so that serum passes from the second separation membrane 36 into moveable serum collection membrane 38. An example of the moveable serum collection membrane 38 includes Grade standard 14 conjugation pad which is made from glass fiber and sold by GE Healthcare/Life Sciences. When a droplet of whole blood sample 22 is placed onto the first serum separation membrane 34, it gets rapidly absorbed due to the hydrophilic nature and the capillary action of the pad. The sample then moves to a red blood cell separation membrane 36 that is made of asymmetric polysulfone, designed to capture the plasma components from whole blood. For the device, a GR grade membrane was used, which provides a plasma yield of >80% and exhibits low non-specific binding, rendering it optimal for use in POC diagnostic devices. The serum sample moves to the c moveable serum collection membrane 38 via the lateral flow-based separation membrane 36. Eventually, when the moveable serum collection membrane 38 is saturated, no further fluid flow is possible, and the flow stops.

A holder 32 holds the first serum separation membrane 34 and the second separation membranes 36 (i.e., sample pad) while a separate moveable holder 40 holds the moveable serum collection membrane or sample collection pad 38. The moveable holder 40 may take the form of an arm or slide that moves the moveable serum collection membrane or sample collection pad 38 between first a first position and a second position as seen in FIGS. 1B and 3A-3D. As seen in FIGS. 1B, 3A, 3B, 3D, in the first position (#1) the moveable holder 40 holds the moveable sample serum collection membrane or sample collection pad 38 against one end the second separation membrane 36 (the end that holds the serum). In the second position (#2), as seen in FIGS. 1B and 3C, the moveable holder 40 holds the moveable sample serum collection membrane or sample collection pad 38 within a test sample holder 42 (e.g., well) having assay reagent(s) 50 contained therein. The one or more assay reagents 50 may be in liquid or dry (e.g., lyophilized) form. The nature of the assay reagents also depends on the particular analyte that is being tested. In one particular example, the assay reagents 50 include malachite green assay reagents (for measuring phosphate concentration). The moveable holder 40 is biased to the first position (#1) using one or more biasing devices 46. The biasing device 46 may include using a pair of magnets or magnetically susceptible material to magnetically attract the sample serum collection membrane or sample collection pad 38 against the second separation membrane 36. Other biasing devices 46 include using a mechanical biasing force such as spring or another resilient member that biases the moveable holder 40 to the first position (#1). The biasing may also be accomplished using a friction fit or the like that holds the moveable holder 40 in the first position (#1). The biasing device 46 may contain detents or the like that secures the moveable holder 40 into position. The biasing device 46 may include a clip or fastener that holds the moveable holder 40 in a specific position (e.g., first position (#1) or second position (#2)). A shim or spacer 48 similar to those described above may be used to keep the moveable holder 40 in the second position (#2) which can be removed. This is illustrated, for example, in FIG. 3C.

The sample serum collection membrane or sample collection pad 38 is then incubated in the test sample holder 42 (e.g., well, reservoir, vessel, container, chamber, or the like) as explained herein for a period of time using the moveable holder device 40 that selectively moves the sample serum collection membrane or sample collection pad 38 into and out of contact with the second separation membrane 36. In one embodiment, magnets 46 are used to bias the sample serum collection membrane or sample collection pad 38 to the second separation membrane 36. During incubation a spacer or shim 48 may be used to dip the same in the test sample holder 42 containing one or more reagents 50 therein for the colorimetric assay and prevent the sample serum collection membrane or sample collection pad 38 from retracting and returning to the first position (#1).

To run the colorimetric assay, the opto-mechanical reader 16 includes one or more light sources 24 such as light emitting diodes (LEDs) that are powered by a battery 26 and control/driver circuitry 27 also contained in the opto-mechanical reader device 16. The light emitting diodes 24 emit light that passes through an optional diffuser 28 and then through the test sample holder 42 and a control sample holder 44. The control sample holder 44 contains, in one embodiment, the assay/reagent solution without exposure to the analyte (e.g., malachite green assay), and is used to compare the light intensity obtained by the camera 14 from the test sample holder 42 as explained herein. The light passing through the test sample holder 42 and a control sample holder 44 is then captured by the camera 14 of the portable electronic device 12. As seen in FIG. 1G, the reader device 16 has a lens or set of lenses 17 disposed along the optical path OP to focus the light transmitted through the test sample holder 42 and a control sample holder 44 onto the camera 14. In some embodiments, the lens 17 may be omitted.

Specifically, in one embodiment, color images 13 of the test sample holder 42 and the control sample holder 44 are then captured by the camera 14 of the portable electronic device 12. The application or software 18 running on the portable electronic device 12 then uses the intensity of the color images 13 of the test sample holder 42 and the control sample holder 44 (seen in FIG. 1E) to determine the concentration of the analyte. Specifically, after interacting with the phosphate in the collected serum and reagent(s) 50, there is a colorimetric change of the contents of the test sample holder 42. The ratio of the colorimetric signal change between the test sample holder 42 and the control sample holder 44 is used to determine the analyte (e.g., phosphate) concentration (e.g., ratio (R) of the intensity of the light transmitted through the test sample holder 42 and the control sample holder 44) as explained herein.

FIGS. 1C and 1D illustrate an alternative embodiment of the system 10. In this embodiment, rather than have paper or membrane components of the paper-based chip 30, these functionalities are incorporated into a single microfluidic chip 60. The microfluidic chip 60 may be formed in plastic, glass, polymers (e.g., polydimethylsiloxane or PDMS), and combinations thereof. As best seen in FIG. 1C, the microfluidic chip 60 includes an inlet 62 into which blood or other liquid sample is loaded into. The inlet 62 is coupled to one or more microfluidic channels 64 that lead to a test chamber, well, or region 66 in the microfluidic chip 60. The test chamber, well, or region 66 may include one or more reagents 50 used to test for the analyte of interest. The one or more reagents 50 may be in liquid or dry (e.g., lyophilized) form. The microfluidic chip 60 may also include a control chamber, well, or region 68 that contains a control sample. The blood that is loaded into the inlet 62 is subject to filtration or separation of blood cells (red blood cells and white blood cells) along the one more microfluidic channels 64. The filtration or separation of blood cells may be accomplished using any number of technologies. For example, microwells located along the microfluidic channels 64 may be used for the sedimentation or collection of blood cells. This would require the pumping/forcing of blood through the microfluidic chip 60 using, for example, a syringe pump or the like. The microfluidic chip 60 may need an optional temporary outlet which is used to recirculate flow within the microfluidic chip 60 to ensure adequate trapping of blood cells (if blood is recirculated). Alternatively, the walls of the microfluidic channel 64 (or even the microfluidic channel 64) may be functionalized or contain a trapping material or substance that filters blood cells leaving blood serum (e.g., porous material used to separate blood serum from raw blood).

FIG. 1D illustrates the microfluidic chip 60 placed in the opto-mechanical reader 16 which is secured to a portable electronic device 12 (e.g. mobile phone). The microfluidic chip 60 is inserted into the opto-mechanical reader 16 and places the test and control chambers, wells, regions 66, 68 along an optical path between the light source(s) 24 and the camera 14 of the portable electronic device 12. The test and control chambers, wells, regions 66, 68 are then optically interrogated as noted above to measure the color intensity of light passing through the respective areas of the microfluidic chip 60.

FIG. 1E illustrates a representative image 13 obtained of the test sample holder 42 and the control sample holder 44. The image 13 may include a single extracted color channel of a colored image 13 of the test sample holder 42 and the control sample holder 44. To calculate the concentration of analyte in the sample, the software 18 in the portable electronic device 12 captures the pixel intensity within the areas of the image 13 that contain the image of the of the test sample holder 42 and the control sample holder 44. This may include smaller sub-regions (e.g., central region of respective holders in images 13), where mean or average pixel intensity for both the test sample holder 42 and the control sample holder 44 can be calculated. For example, the mean intensity of the spots may include a region of interest (e.g., 200 by 200 pixels). The mean intensity of this spot corresponding to the sample was divided by the control mean intensity within its corresponding spot to obtain the intensity ratio. The software or application 18 may contain one or more calibration curves, functions, or look-up tables that are stored or accessible by the portable electronic device 12 to determine the concentration of the analyte (e.g., serum phosphate) using the corresponding calibration curve, function, or look-up table. The results may then be reported to the user on the display of the portable electronic device 12 as seen in FIG. 1E.

Experimental

Design and Optimization of the Paper-Based Phosphate Sensor

One of the crucial challenges in measuring serum samples for POC analysis is the difficulty in efficiently separating and collecting serum from whole blood in precise quantities. This approach addresses this challenge by using a paper-based microfluidic chip 30 as best shown in FIGS. 1A, 1B, 1H, 2A, 2B which can efficiently separate serum from small quantities of blood. This paper-based blood separation chip 30 is composed of a sample pad (first separation membrane 34), a red blood cell separation membrane (second separation membrane 36), and a moveable serum collection membrane 38 (sample collection pad). When a droplet of whole blood sample is placed onto the sample pad or first separation membrane 34, it gets rapidly absorbed due to the hydrophilic nature and the capillary action of the pad 34. The sample then moves to a red blood cell second separation membrane 36 that is made of asymmetric polysulfone, designed to capture the plasma components from whole blood. For the device, a GR grade membrane was used, which provides a plasma yield of >80% and exhibits low non-specific binding, rendering it optimal for use in POC diagnostic devices. The serum sample moves to the moveable serum collection membrane 38 or collection pad via the lateral flow-based separation membrane 36. Eventually, when the moveable serum collection membrane 38 is saturated, no further fluid flow is possible, and the flow stops. These engineered features allow for consistent collection of a fixed amount of serum from a single drop of whole blood (~20-50 µL).

Figure 4:
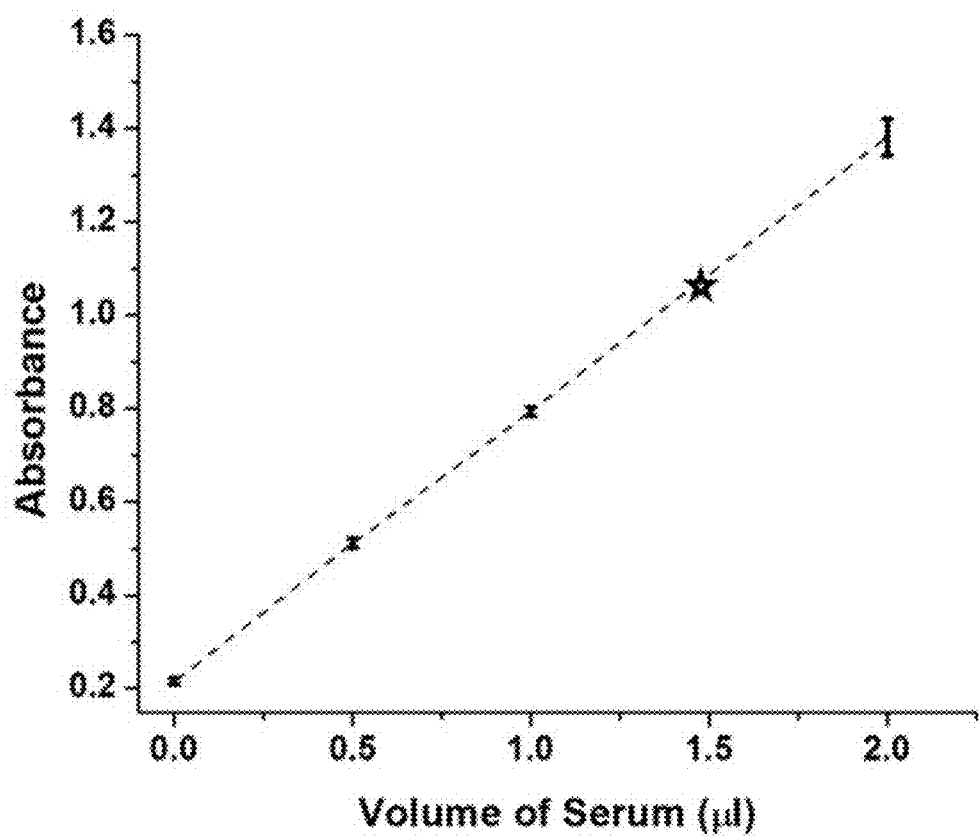
FIG. 4 illustrates the determination of serum volume collected in the collection pad. A calibration curve was created by adding different amounts of serum (in water) with the reagent. The star denotes the absorption from reagent upon interaction with the collection pad, thus indicating its volume. The measurements were performed in triplicates and the standard deviation was calculated based on the individual measurements.

An important characteristic of the moveable serum collection membrane 38 is its low cross-reactivity with the malachite green assay. This assay contains malachite green dye and an acid-molybdate solution, where the presence of free orthophosphates leads to the formation of a phosphomolybdate complex, resulting in a colorimetric change. Several paper materials were screened such as nitrocellulose membranes and fiberglass-based conjugation pads as candidates for the moveable serum collection membrane 38. Finally, Grade standard 14 conjugation pad was selected as it was found to have the least reactivity with the malachite green assay. In order to precisely maintain the pressure between the second separation membrane 36 and the moveable serum collection membrane 38, a two-part holder 40 was designed, consisting of a blood separation holder 32 and the collection membrane 38 holder 40, as seen in FIGS. 1H, 3A-3D. The blood separation holder 32 holds the serum separating chip 30, and the collection membrane 38 (i.e., collection pad 38) is attached to the moveable holder 40. Two magnets 46 (best seen in FIGS. 3A-3D) were used as the biasing devices 46 to maintain a uniform and constant pressure between the chip 30 and the collection membrane 38. The volume of serum gathered using the collection membrane 38 was first characterized by creating a calibration curve using different volumes of serum as shown in FIG. 4. It is estimated that, on average, the collection membrane 38 can hold ~1.55 µL of serum, with an error of less than 10% (~0.15 µL).

Once the serum is collected in the collection membrane 38, the moveable holder 40 is manually lowered into the test sample holder 42 (e.g., a sample well) containing water, and the malachite green reagent is added to this well. The collection membrane 38 is passively incubated in this well for thirty (30) min before being withdrawn by moving the holder 40 in the opposite direction (or letting the holder 40 automatically in response to the biasing device(s) 46). The pad holder 40 is held in place during the entire incubation phase by an adaptor or spacer 48. Upon the completion of the reaction, the adaptor or spacer 48 is pulled out to release the pad holder 40, which is magnetically retracted back. For each serum phosphate measurement, two separate sample holders 42, 44 containing the malachite green reagent were used, with one holder 44 serving as a control and the other holder 42 for the serum sample. After interacting with the phosphate in the collected serum, there is a colorimetric change of the reagent. The ratio of the colorimetric signal change between the control 44 and sample 42 was used to determine the phosphate concentration using a mobile phone-based reader 16. Each test was performed using two different volumes of water and reagent in order to cover a clinical dynamic range of up to ~10 mg/dL of serum phosphate concentration.

Calibration and Testing of the Mobile Phone-Based Assay Reader

The assay quantification was performed automatically using a mobile phone-based reader 16 that holds the test sample holder 42, control sample holder 44, as well as the serum separator chip 30, as shown in FIGS. 1A, 1B, 1F, 1G, 1H, and 3A-3D. After completion of the measurement, the serum separator chip 30 and the sample/control holders 42, 44 containing the reagent need to be discarded and replaced with new ones. The optomechanical attachment 16, weighing ~400 g, is fitted with two different LEDs 24 and a diffuser 28 to ensure uniform light intensity at the test sample holder 42 and control sample holder 44.

Figure 5A:
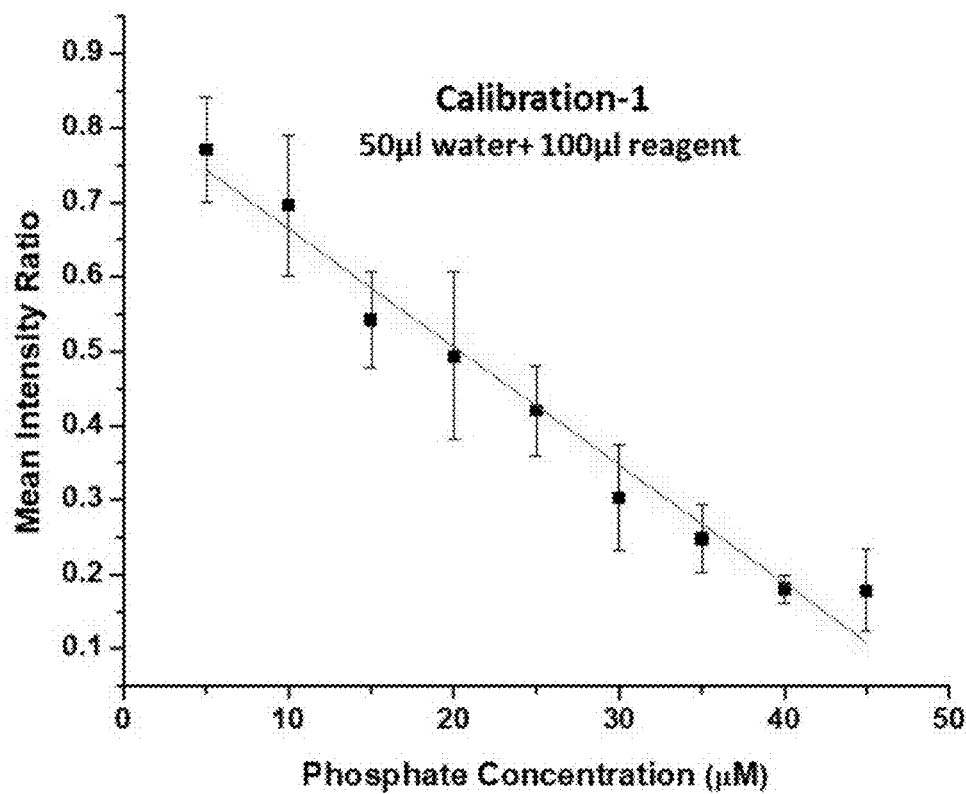
FIGS. 5A and 5B illustrate calibration curves using phosphate standards and two different amounts of reagents. Calibration-1 was performed by adding 100 μl reagent to 50 μl water/phosphate standard. Calibration-2 was performed by adding 200 μl reagent to 100 μl water/phosphate standard. The measurements were performed in triplicates.
Figure 5B:
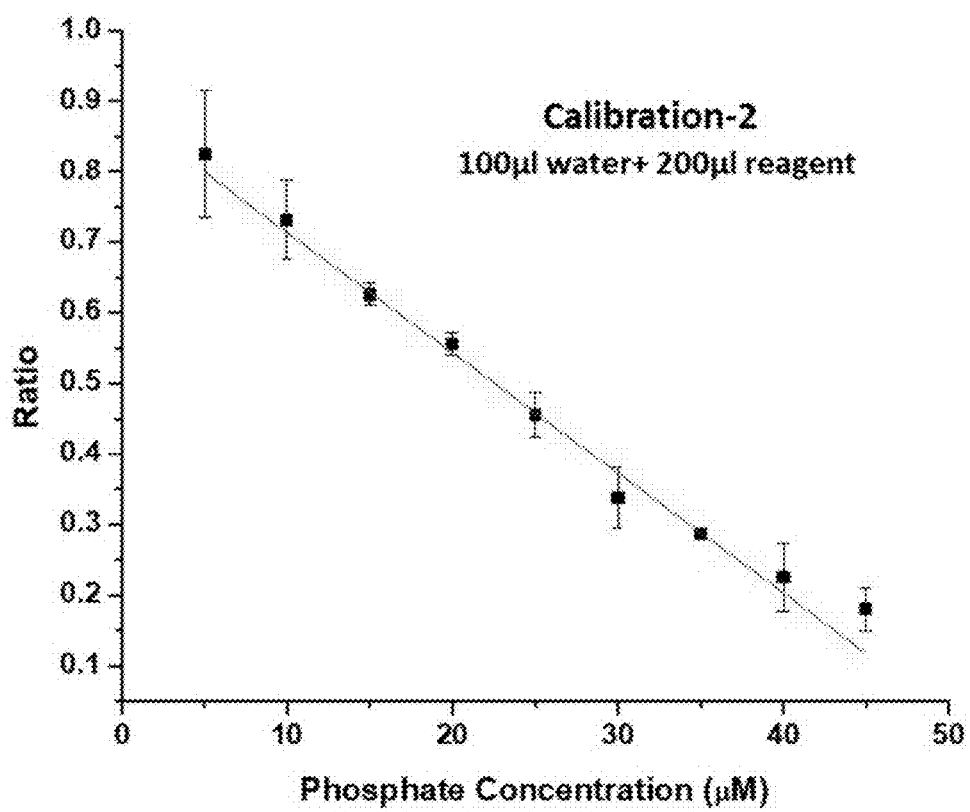

Two different calibration curves were created with known amounts of phosphate using two different volumes of standard and reagent solutions (calibration-1: 50 µl water/standard+100 µl reagent and calibration-2: 100 µl water/standard+200 µl reagent), as shown in FIGS. 5A and 5B, respectively. The calibration curves were created by taking the ratio (R) of the intensity of the light transmitted through the test sample holder 42 (e.g., well) and the control sample holder 44 (e.g., well), and were used for the automated determination of the phosphate concentration in an unknown blood sample. The phosphate value is calculated based on the slope (S) and y-intercept (Y) of the linearly fitted calibration curve, i.e., $$\text{Serum Phosphate} = \frac{R - Y}{S} \times K \qquad \text{Eq. (1)}$$

where K is an empirical constant used to incorporate the dilution factor of the serum that is tested, and convert the concentration unit from µM to mg/dl. The first calibration curve, which is based on an assay utilizing 50 µl water and 100 µl reagent, enables the measurement of up to 4.5 mg/dl serum phosphate concentration. The second calibration curve is used to increase this range to 10 mg/dl by diluting the serum (i.e., utilizing 100 µl water and 200 µl reagent). These two calibration curves have two separate K values associated with them. The parameters in Eq. (1) as well as the error in the serum volume in the collection pad 38 were used to numerically estimate the overall error in the measurements. For example, an error of ~0.50 mg/dl is estimated based on the first calibration curve and ~0.98 mg/dl based on the second calibration curve for a serum phosphate concentration of 4.5 mg/dl. The calibration curves may be stored in the application or software 18 that is run on the portable electronic device 12.

Proof of concept experiments to test the system 10 were performed by measuring the serum phosphate levels from pediatric end-stage renal disease patients receiving hemodialysis treatments three times a week. Whole blood samples were obtained at baseline (just before starting the hemodialysis treatment) and during the three-hour treatment, as per protocol. During each hemodialysis treatment, whole blood was collected from the pre-dialyzer side of the hemodialysis circuit. Collecting blood at different time points during the hemodialysis session allows one to assess blood samples with a wide range of phosphate concentrations, as serum phosphate is usually high in ESRD patients at the beginning of hemodialysis treatments, then decreases as the treatment proceeds. Each whole blood sample was collected in heparin coated serum separator tubes and tested using the system 10.

Figure 6:
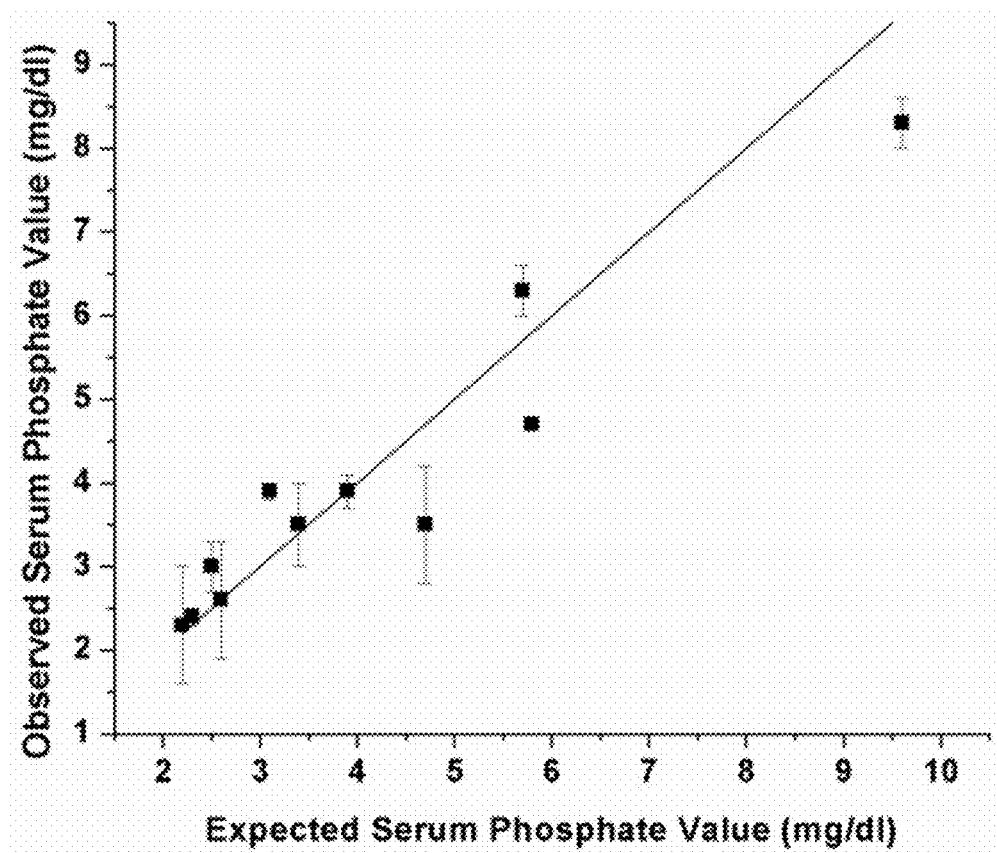
FIG. 6 illustrates patient testing results. Comparison of the mobile sensor's serum phosphate measurement results against the results of a laboratory instrument (Alfa-Wasserman ACE® Alera Systems analyzer), which yields r=0.95; P<0.001. The solid line shows y=x. Each measurement was performed in triplicate.

Approximately 40 µl blood was used per test and the tests were performed in triplicates. The rest of the whole blood sample was used to extract the serum via centrifugation and stored in −80° C. freezer for independent laboratory validation at a later time point. Serum phosphate levels of three patients measured at different time points using the mobile phone-based device 10 (FIG. 6) showed strong correlation with independent laboratory measurements with a Pearson correlation coefficient of r=0.95 and p<0.001. A fourth patient was also tested while undergoing dialysis, however it was observed that a significant amount of precipitation in the reagent upon reacting with the serum. The reason for this particular observation is unclear, however this could have been due to e.g., an interference from a particular drug that the patient took, or high amount of serum proteins interfering with this assay.

Figures 2A, 2B:
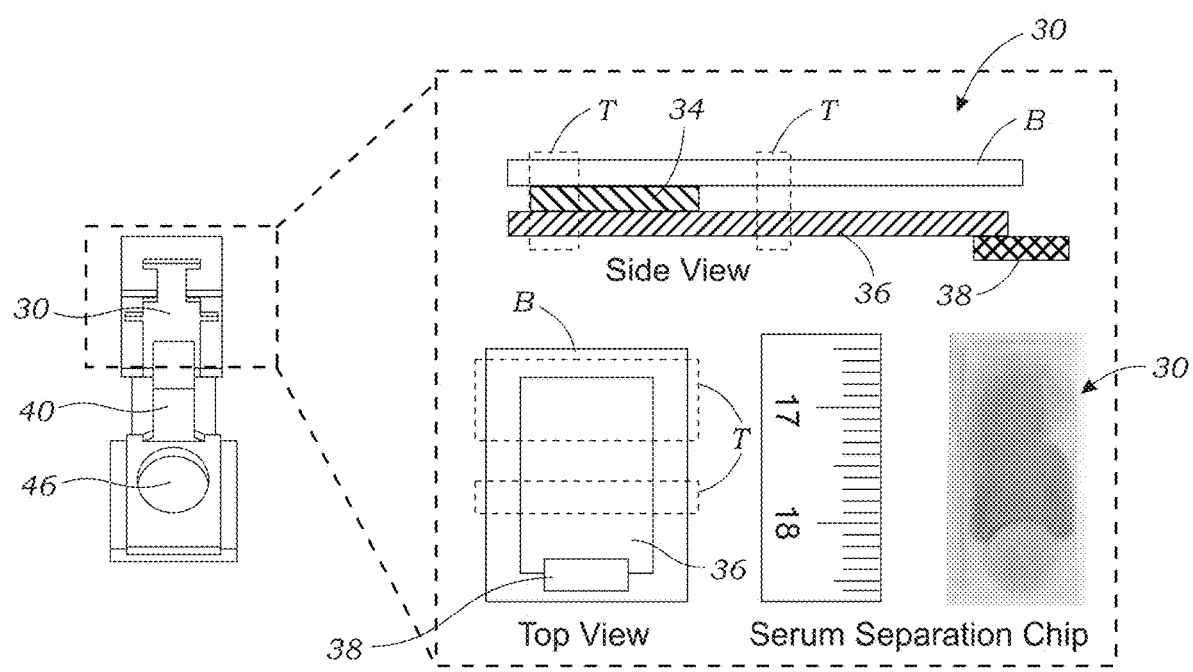
FIG. 2A illustrates the two-part holder for the paper-based chip.
FIG. 2B illustrates a schematic of the serum separation chip. The labels are as follows: Plastic adhesive backing B, Sample pad or membrane 34 (Fusion 5), Membrane 36 (VPS GF/GR), Adhesive tape T, Collection pad 38. A photograph of the serum separation using the paper-based chip is also shown on the right.

Serum Separation Chip:

The serum separation chip 10 was constructed as a lateral flow device as shown in FIG. 2B. A plastic adhesive backing was used to support the structure. A 2 mm hole was punched out on the plastic backing and covered with the sample pad or first separation membrane 34. A 3 mm diameter circle of Fusion 5 (GE Healthcare Biosciences Corporation) was used as the sample pad or first separation membrane 34. The Fusion 5 membrane is a single layer matrix membrane that is made from a hydrophilic material. The GR Plasma Separation Membrane (4 mm×8.75 mm, Pall Company), that acts as the filter or second separation membrane 36, was placed directly on top of the sample pad 34 ensuring no leakage from the sample pad sides. Additionally, a piece of 6 mm wide adhesive tape was used to completely seal the area below the sample pad. A second piece of tape (2 mm wide) was used below the first one at a distance of ~2-3 mm to prevent any blood from leaking onto the collection pad 38. The tape and the membranes were precisely cut using a laser cutter.

Preparation of the Serum Separation Device:

A two-part device was 3D printed and used to hold the serum separation chip 30. The casing consists of two separable components. The lower half is the chip holder 32, and the upper half is the sample collector 40. A Grade standard 14 conjugation pad (GE Healthcare Biosciences Corporation) was used as the moveable serum collection membrane or collection pad 38. Two magnets 46 were used to maintain uniform contact between the collection pad 38 and the plasma separation membrane 36. This ensures that there is a good flow of serum from the membrane 36 to the collection pad 38, and that the collection pad 38 can be fully saturated.

Serum Separation:

Several different blood volumes were tested, ranging from 10 µl to 100 µl. The system 10 worked consistently for a volume range of 10 µl to 60 µl. Thus, for this application, 40 µL of blood was used which was introduced onto the collection pad 38 of the device. To ensure the complete saturation of the collection pad 38, the device was let to sit for 10 min. This allowed the sample to flow through the membranes 34, 36 and for the collection pad 38 to become completely saturated with serum. However, the serum separation often occurs more quickly, and saturation of the collection pad 38 was observed within 5 min. After 10 min, the collection pad 38 is manually lowered into the test sample holder 42 and set for 30 min (passive reaction time), using a manual attachment, for the reaction to complete.

The volume of serum collected in the serum collection membrane or collection pad 38 was determined by using a calibration curve (FIG. 4). This calibration curve was created by recording the absorbance of the reagent (100 µL) upon interaction with a fixed amount of serum diluted in 50 µL water. These measurements were performed in a 96 well plate using a standard plate reader. The volume of serum in the collection pad 38 was determined by comparing the absorbance due to the interaction of the serum-soaked collection pad 38 in water and reagent, with the calibration curve shown in FIG. 4.

Determination of Phosphate Concentration:

Following a 30-minute incubation, the collection device was removed by detaching the attachment. The colorimetric change was recorded using the mobile phone camera 14 as illustrated in FIGS. 1A, 1E, 1F, and 1G. The mobile phone reader 16 has two 3D printed parts that hold the phone 12 and wells 42, 44 in place while imaging. Two battery-powered LEDs 24 (620 nm wavelength) were used as the illumination source. Light from the LEDs 24 passed through a diffuser 28, followed by a narrow channel to irradiate the wells placed at the end of the channel. The phone 12 was placed at a distance of 5 cm from the sample to ensure optimal sensitivity. For this application, a Nokia Lumia mobile phone 12 was used, which was placed upside down in the holder so that the cell phone camera, lens 17, sample, and LEDs 24 were properly aligned. The phone camera settings were manually set to 1/8000 exposure and infinity focus.

The images 13 were analyzed by first splitting the color channels and using the red channel (other channels could also be used for other analytes). The mean intensity of the spots was calculated using a small region of interest (200 by 200 pixels), and the same was done for the control. The mean intensity of the spot corresponding to the sample was divided by the control mean intensity to obtain the intensity ratio. The assay was performed by placing the sample well (test sample holder 42) on the right and the control well (control sample holder 44) to its left. The mean intensity ratio was used to determine the phosphate concentration by using pre-prepared calibration curves.

Colorimetric Phosphate Assay:

A malachite green assay (Bioassay Systems, DIPI-500) was used to determine the phosphate concentration of blood samples. DIPI-500 showed no interference with the selected paper materials, and additionally demonstrated the least interference with serum proteins. Two different protocols with DIPI 500 were used for this purpose. The collection pad 38 was first put in either 50 µl or 100 µl water. Then, either 100 µl (with 50 µl water) or 200 µl (with 100 µl water) of the malachite green assay was added, and the mixture was allowed to incubate for 30 minutes. The absorbance was measured using the cell phone-based reader 16 and cross-validated using a standard plate reader. The initial measurements were performed using 50 µl water (with 100 µl reagent) as it is more sensitive at lower serum phosphate concentrations; however, the upper limit of detection of the assay with this ratio is 5 mg/dl. If the result of the first test indicated a value greater than 4 mg/dl, then the measurements were repeated using 100 µl water (with 200 µl reagent). If the second test resulted in a value <4.5 mg/dl, then the first measurement result with 50 µl water was recorded. Otherwise the result of the second test with 100 µl water was recorded. For serum phosphate values of <4.5 mg/dl, the assay with 100 µl reagent (50 µl water) was preferred based on the calibration curve-1 as it has a lower error compared to the second calibration curve. The upper limit of detection of the specific malachite green assay that was tested is 50 µM phosphate. Thus, upon diluting the serum (1.55 µl) in water (50 µl), a dilution of ~32 fold is created, which sets the upper limit of detection to ~5 mg/dl of phosphate concentration in serum. However, by using 100 µl of water and diluting 1.55 µl of serum in it, the dilution was increased to ~64 fold, thus enabling serum phosphate measurements of up to ~10 mg/dl concentration.

Preparation of the Calibration Curves:

The calibration curves were prepared using phosphate standards. The standards were prepared from a 1 mM phosphate solution. For this application, a 50 µM solution was first prepared and then used it to generate the following concentrations: 5, 10, 15, 20, 25, 30, 35, 40, and 45 µM, in addition to the control sample. The accuracy of the dilution was checked by comparing the 30 µM sample, that was prepared via serial dilution, with commercially available samples of equal concentration. A slight difference in absorbance was observed between the two 30 µM samples (commercial vs. the one prepared via serial dilution), and this difference was used to accordingly adjust the other points on the calibration curve. Two different calibration curves (FIGS. 5A and 5B) were prepared by adding 100 µl reagent to 50 µl phosphate standard (Calibration-1) and 200 µl reagent to 100 µl phosphate standard (Calibration-2). These calibration curves were prepared by placing the sample well (test sample holder 42) on the right and the control well (control sample holder 44) to its left.

Validation of the Serum Phosphate Measurements Using a Laboratory Instrument:

To provide ground truth comparison measurements, the serum was separated from whole blood for validation studies by centrifuging blood at 10,000 g for 10 min. The resultant serum was removed from the serum separator tube and aliquoted into new tubes. These serum samples were stored at −80° C. The serum samples were then delivered to a central chemistry lab, where the serum phosphate concentration was measured using an Alfa-Wasserman ACE® Alera Systems analyzer. The correlation between serum phosphate concentrations measured by the central chemistry lab and by the mobile sensor was assessed using SigmaPlot 12.5 (San Jose, Calif.).

Patient Recruitment and Consent:

Patients with end-stage renal disease were recruited from the Davita/Century City dialysis unit. This study was approved by UCLA Human Subjects Protection Committee, (IRB #10-000886) and informed consent was obtained from each patient. Two patients signed the consent themselves and two others were signed by their parents/guardian because they were <18 years.

A cost-effective POC-based system 10 is disclosed that is capable of accurately measuring serum phosphate concentrations by combining a paper-based microfluidic chip 30 and a smartphone-based reader 16. A small quantity of blood is loaded onto the lateral flow microfluidic chip 30 that separates the serum from whole blood. A collection pad 38 is used to collect the serum sample, which is then transferred to a well 42 containing malachite green reagent. The colorimetric change of the solution is recorded using a Smartphone 12 and is used to determine the serum phosphate concentration. This device was tested using clinical samples from patients undergoing dialysis. The results demonstrated a strong correlation between the independent laboratory measurements and the mobile sensor readings (r=0.95, p<0.001), demonstrating the ability of this cost-effective POC system 10 to accurately measure serum phosphate concentrations. This system 10 can benefit a vast number of individuals, including patients with CKD/ESRD, as well as others who need frequent monitoring of serum phosphate levels.

While embodiments of the present invention have been shown and described, various modifications may be made without departing from the scope of the present invention. For example, while the sample receiving pad has been described herein as containing a plurality of membrane or pad layers, the sample receiving pad may include a single pad/layer or multiple pads/layers. The invention, therefore, should not be limited except to the following claims and their equivalents.

What is claimed is:

1. A portable colorimetric assay system comprising:
an opto-mechanical reader configured to be detachably mounted to a mobile phone having a camera or other camera-containing portable electronic device, the opto-mechanical reader comprising one or more light sources configured to illuminate a test sample holder having assay reagent(s) contained therein and control sample holder disposed in the opto-mechanical reader along an optical path aligned with the camera of the mobile phone or other camera-containing portable electronic device;
one or more serum separation membranes disposed in the opto-mechanical reader and defining a sample receiving pad configured to receive a blood sample; and
and a moveable serum collection membrane configured to contact the sample receiving pad in a first position and moveable to a second position where the serum collection membrane is disposed inside the test sample holder in the second position.

2. The portable colorimetric assay system of claim 1, wherein the one or more light sources comprises a plurality of light sources configured to illuminate the test sample holder and/or the control sample holder.

3. The portable colorimetric assay system of claim 1, wherein the moveable serum collection membrane is supported by a holder biased toward the first position.

4. The portable colorimetric assay system of claim 3, wherein biasing means biases the holder toward the first position.

5. The portable colorimetric assay system of claim 3, wherein a pair of magnets biases the holder toward the first position.

6. The portable colorimetric assay system of claim 1, further comprising a shim or spacer that holds the holder to position the moveable serum collection membrane in the second position.

7. The portable colorimetric assay system of claim 1, further comprising software or an application executed by the mobile phone or other camera-containing portable electronic device for calculating an intensity ratio based on one or more image(s) obtained of the test sample holder and the control sample holder.

8. The portable colorimetric assay system of claim 7, wherein the intensity ratio is calculated by an average or mean intensity ratio obtained from respective spots within an image or images of the test sample holder and the control sample holder.

9. The portable colorimetric assay system of claim 1, wherein the one or more serum separation membranes comprises a first membrane configured to receive blood and promotes flow in a first direction and a second membrane disposed against the first membrane and configured to promote flow of blood serum in a second direction generally orthogonal to the first direction.

10. A method of using the portable colorimetric assay system of claim 1, comprising:
loading a blood sample onto the sample receiving pad;
contacting the moveable serum collection membrane with the sample receiving pad in the first position;
moving the moveable serum collection membrane to a second position within the test sample holder;
maintaining the moveable serum collection membrane in the second position for an elapsed period of time to react with the contents of the sample holder with one or more reagents contained in the test sample holder;
illuminating the test sample holder and the control sample holder with the one or more light sources;
acquiring one or more images of the test sample holder and the control sample holder with the camera of the mobile phone or other camera-containing portable electronic device; and
calculating with software or an application executed by the executed on the mobile phone or other camera-containing portable electronic device a concentration of an analyte contained in the test sample holder based on a ratio of intensity of light in the one or more images of the test sample holder and the control sample holder.

11. The method of claim 10, wherein the analyte comprises phosphate.

12. The method of claim 10, wherein the ratio of intensity of light in the one or more images of the test sample holder and the control sample holder comprises extracting the mean intensity of respective spots within the image(s) of the test sample holder and the control sample holder.

13. The method of claim 10, wherein the software or application compares the ratio of intensity of light to a calibration curve, function, or look-up table and outputs a corresponding analyte concentration.

14. A portable colorimetric assay system comprising:
a microfluidic chip configured to receive a blood sample at an inlet and separate blood serum from the blood sample into a test sample region having assay reagent(s) contained therein of the microfluidic chip via one or more microfluidic channels or capillaries, the microfluidic chip further comprising a control sample region; and
an opto-mechanical reader configured to be detachably mounted to a mobile phone or other camera-containing portable electronic device, the opto-mechanical reader comprising one or more light sources configured to illuminate the test sample region of a microfluidic chip and the control sample region of the microfluidic chip when the microfluidic chip is disposed in the opto-mechanical reader along an optical path aligned with the camera of the mobile phone or other camera-containing portable electronic device.

15. The portable colorimetric assay system of claim 14, wherein the microfluidic chip comprises a plurality of microfluidic channels or capillaries connecting the inlet to the test sample region.

16. The portable colorimetric assay system of claim 14, wherein the one or more microfluidic channels contain separation media disposed thereon or therein.

17. A method of using the portable colorimetric assay system of claim 14, comprising:
loading a blood sample into the inlet of the microfluidic chip;
illuminating the test sample region and the control sample region with the one or more light sources;
acquiring one or more images of the test sample region and the control sample region with the camera of the mobile phone or other camera-containing portable electronic device; and
calculating with software or an application executed by the executed on the mobile phone or other camera-containing portable electronic device a concentration of an analyte contained in the test sample based on a ratio of intensity of light in the one or more images of the test sample region and control sample region.

18. The method of claim 17, wherein the analyte comprises phosphate.

19. The method of claim 17, wherein the ratio of intensity of light in the one or more images of the test sample holder and the control sample holder comprises extracting the mean intensity of respective spots within the image(s) of the test sample holder and the control sample holder.

20. The method of claim 17, wherein the software or application compares the ratio of intensity of light to a calibration curve, function, or look-up table and outputs a corresponding analyte concentration.

* * * * *